United States Patent [19]

Lalonde

[11] Patent Number: 5,578,032

[45] Date of Patent: Nov. 26, 1996

[54] BONE CLAMP

[75] Inventor: Donald H. Lalonde, Saint John, Canada

[73] Assignee: Accurate Surgical & Scientific Instruments Corporation, Westbury, N.Y.

[21] Appl. No.: 359,972

[22] Filed: Dec. 20, 1994

[51] Int. Cl.$^6$ .................................................. A61B 17/60
[52] U.S. Cl. .............................. 606/54; 606/72; 606/205; 606/207
[58] Field of Search ................................. 606/53, 54, 57, 606/58, 86, 90, 105, 205, 207, 208, 72

[56] References Cited

U.S. PATENT DOCUMENTS

| | | | |
|---|---|---|---|
| 3,828,791 | 8/1974 | Santos | 606/207 |
| 4,723,548 | 2/1988 | Lalonde . | |
| 4,997,434 | 3/1991 | Seedhom et al. | 606/53 |
| 5,133,724 | 7/1992 | Wilson, Jr. et al. | 606/208 |

FOREIGN PATENT DOCUMENTS

| | | | |
|---|---|---|---|
| 1082412 | 3/1984 | U.S.S.R. | 606/54 |

OTHER PUBLICATIONS

Cover page and page containing item 64–01100 of Leibinger catalog (date unknown).
Cover and pp. 356 and 357 of Miltex Surgical Instruments catalog (date unknown).
Pp. 69 and 80–83 of Link Instrumentation for Hand Surgery catalog (date unknown).
Catalog page on Lowman clamps (date unknown).
Catalog page on Backhaus clamps (date unknown).
Pp. 208 and 209 from Codman catalog (date unknown).

*Primary Examiner*—Guy Tucker
*Attorney, Agent, or Firm*—Jordan and Hamburg

[57] ABSTRACT

A bone clamp for insertion into a surgical incision perpendicular to a bone fracture has a ratchet mechanism. The bone clamp includes a scissor portion and a clamping portion. The scissor portion includes a pair of scissor arms, pivotally connected to one another, each having a finger loop at one end. Cooperating components of the ratchet mechanism are carried on each scissor arm, permitting a stepwise reduction in distance between the loops and between terminal ends of the scissor arms through the pivotal connection while preventing separation of the loops. The clamping portion includes a first elongated member pivotally connected at one of its ends to the terminal end of one of the scissor arms with a gripping point at another end. A second elongated member is pivotally connected to the terminal end of the other scissor arm. The first and second elongated members are slidably mounted to one another along their longitudinal axes. A hooked portion is disposed at the free end of the second elongated clamp member, terminating in a gripping point in alignment with, and opposing, the gripping point of the first elongated member. By mounting a pair of bone clamps in accordance with the invention side by side on a slide bar, with at least one of the bone clamps slidably mounted and securable at desired locations along the slide bar, fractured bone segments may be approximated.

14 Claims, 5 Drawing Sheets

BONE CLAMP

BACKGROUND OF THE INVENTION

The present invention relates to bone clamps used in surgical procedures to urge broken bones into alignment for the proper mending thereof, and for the fixing of plates to fractured bones so the plates may be screwed to the bones to maintain proper positioning thereof following reduction or approximation of the fracture.

There are commercially available a variety of bone clamps for reducing bone fractures, i.e. the urging of fractured portions of a bone into proper alignment with one another. These generally fall into two categories which include parallel and perpendicular types, designated in accordance with the orientation of the axis of the device with respect to the axis of the fracture. A parallel bone clamp approaches the axis of the fracture parallel with its own axis. A perpendicular bone clamp approaches the axis of the fracture with its own axis perpendicular to the axis of the fracture.

Included among the more commonly used parallel bone clamps are the Verbrugge, the Lange, the Kern, the Ulrich, the Lambotte, the Seidel, and the Lanenbeck. Each of these clamping devices utilizes a ratchet mechanism to apply and maintain pressure on the severed portions of the bone being urged into mutual contact alignment. Although effective for a variety of applications, the above mentioned bone clamps occupy too much space to be used in the repair of small bone fractures, such are those of the metacarpal and phalanx. In reducing such fractures, the clamp must be oriented with its axis in parallel to the bone fracture and cannot be inserted into the confining wound because of the close proximity of the adjacent metacarpals or metatarsals. Similarly, in repair of fractures to the phalanx, the extensor mechanism greatly impedes insertion of such parallel bone clamps into the wound.

The instrument currently used most often for the repair of small bone fractures is the common towel clip. Deriving its name from its original designed purpose of holding towels together in a sterile field, the towel clip was never intended for use in bone fracture surgery. The towel clip falls into the category of parallel type bone clamps, with its shape resembling a pair of miniature ice tongs having a pair of sharp, opposing points which may be brought together by scissor action. A ratchet mechanism assists in applying and maintaining pressure on a fractured bone interposed between the points. It has found application as a device used in small bone reductions because it occupies less space than most parallel bone clamps, and is commonly available. In addition, its rugged design permits the application of relatively large forces required to reduce bones and the two sharp points reliably grasp the opposed bone surfaces without slipping. There are however two main disadvantages associated with the towel clip. Because the towel clip functions as a parallel bone clamp, it occupies too much space for many smaller procedures. Also, many towel clips have ratchet bars of insufficient length, allowing the ratchet teeth to disengage when the towel clip is open during a bone reduction.

Perpendicular bone clamps currently available include such devises as the Lowman-Gerster and the Lowman-Hoglund bone clamps. Also included is the Bunnell-Howard arthrodesis bone clamp. By permitting insertion thereof into the wound incision perpendicular with the axis of the fracture, such instruments can be used to more effectively than parallel bone clamps in reduction of bone fractures in confined regions. The above bone clamps, however, utilize a screw mechanism to tighten the jaws of the clamp for reduction of the fractured bone held therebetween. As a result, the reduction procedure cannot be performed with the speed permitted by use of a ratchet mechanism, nor is power delivered as efficiently and easily. In addition, the screw mechanism often requires the use of both hands, whereas the use of only one hand is preferable.

OBJECTS AND SUMMARY OF THE INVENTION

Accordingly, it is an object of the invention to provide a bone clamp which overcomes the drawbacks of the prior art.

It is a further object of the invention to provide a bone clamp which may be inserted into a surgical incision perpendicular to a bone fracture to occupy minimal space in the wound.

It is a still further object of the invention to provide a perpendicular bone clamp which utilizes a ratchet mechanism for simple and efficient operation.

It is yet a further object of the invention to provide a bone clamp which is economical, yet rugged enough to withstand the forces of bone reduction without bending.

It is yet a further object of the invention to provide a bone clamp which when used in pairs, slidably mounted side by side on a slide bar, can be used to approximate bone fractures while occupying minimal space in an incision.

Briefly stated, there is provided a bone clamp, with a ratchet mechanism, which may be inserted into a surgical incision perpendicular to a bone fracture. The bone clamp includes a scissor portion and a clamping portion. The scissor portion includes first and second scissor arms, pivotally connected to one another between first and second ends of each. Loops are provided at the first end of each scissor arm for receiving a thumb and an opposing finger, such as a forefinger. Cooperating components of the ratchet mechanism are carried on each scissor arm proximate the first end of each, permitting a stepwise reduction in distance between the loops and between the second ends of the scissor arms through the pivotal connection. The ratchet mechanism also prevents separation of the loops. The clamping portion includes first and second clamp members. The first clamp member is an elongated pin, pivotally connected at a first end to the second end of the first scissor arm. A second end of the first clamp member is a sharp point or other surface configuration suitable for gripping bone. The second clamp member is slidably mounted in said first clamp member with the longitudinal axes of each in parallel alignment. A hooked portion is disposed at the second end of the second clamp member, terminating in a point or other suitable bone gripping surface in alignment with, and opposing the gripping surface of the first clamp member.

In the preferred embodiment, the second clamp member includes in its structure an elongated tube of constant internal dimension, in which the first clamp member is slidably received. The elongated tube of the second clamp member is pivotally attached at a first end to the second end of the second scissor arm. At a second end of the elongated tube, the aforementioned hooked portion is integral with, or fixedly attached to the elongated tube. The hooked portion terminates in a point, or other suitable bone gripping configuration, facing the opening in the second end of the elongated tube and in alignment with the gripping surface on the second end of the first clamp member.

In a further embodiment, a pair of bone clamps in accordance with the present invention are slidably mounted on a slide bar, side by side, preferably in a parallel fashion, together comprising a bone approximator. One or both bone clamps are slidable to a desired location along a substantial length of the slide bar. The bone approximator further includes means for securing each slidable bone clamp at the desired location. Use of the bone approximator incorporating a pair of perpendicular bone clamps in accordance with the present invention, permits approximation of a crosswise fracture while requiring minimal space within the surgical incision. The separated segments of bone are each gripped with one of the pair of bone clamps. By sliding the bone clamps together, the segments gripped between opposed gripping surfaces can be approximated for mending thereof. The bone clamps may then be secured in position along the slide bar, preventing movement of the bone segments, until the mending procedure is complete.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
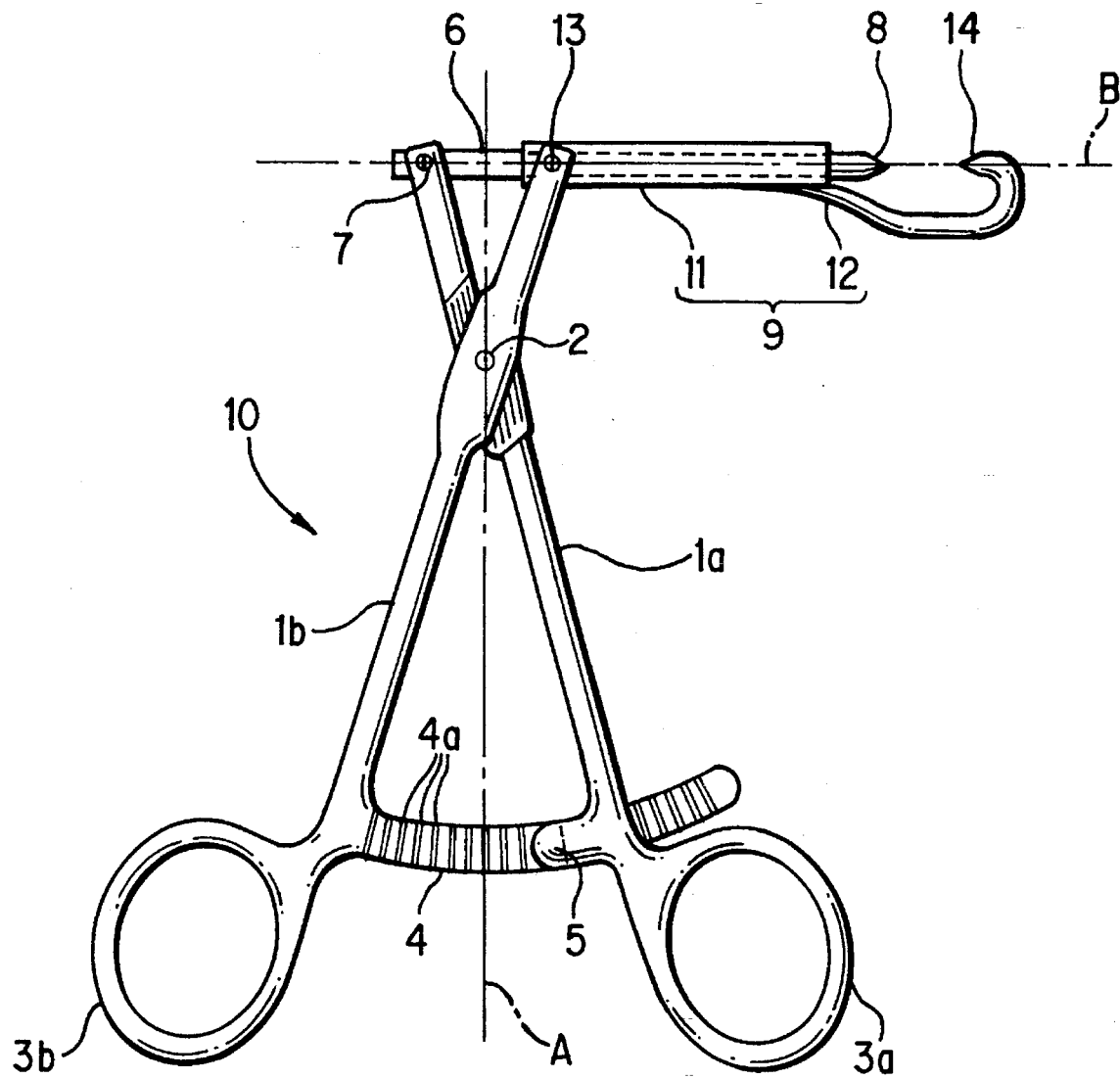
FIG. 1 is a side elevation of the bone clamp in accordance with the present invention.

Referring now to FIG. 1, there is shown, generally at 10, a bone clamp, in accordance with the invention. The components of bone clamp 10 are constructed of a suitable material typically used for instruments of similar application. Generally, such materials will allow sterilization, resist corrosion, and have good strength characteristics, such as, for example, stainless steel.

A pair of scissor arms 1a and 1b are connected through a scissor pivot 2. Finger loops 3a and 3b are provided at respective ends of scissor arms 1a and 1b for transmission of a hand motion to scissor arms 1a and 1b. In the preferred case, finger loops 3a and 3b are closed loops, allowing the user to effect a closure of bone clamp 10 wherein finger loops 3a and 3b are brought together and scissor arms 1a and 1b move to a position in which each approximates a common longitudinal scissor axis A. Similarly, opening of bone clamp 10 is effected by movement increasing the distance between finger loops 3a and 3b. Bone clamp 10 in FIG. 1 is shown in an open position. A ratchet arc 4 extends from scissor arm 1b substantially along a common plane of bone clamp 10, oriented to cooperate with a corresponding ratchet cog 5 on scissor arm 1a. Ratchet arc 4 comprises a series of teeth 4a, each having a face perpendicular to ratchet arc 4 on a side facing finger loop 3b, and a sloped face on the other side. Ratchet cog 5 comprises a single tooth having a profile similar to teeth 4a, the perpendicular face of which faces finger loop 3a. This configuration allows stepwise closure of scissor arms 1a and 1b as ratchet cog 5 slips over the sloped surface of each of teeth 4a on ratchet arm 4, while the perpendicular surfaces on both ratchet cog 5 and teeth 4a engage to prevent opening of scissor arms 1a and 1b. Opening of bone clamp 10 is accomplished by a twisting action sufficient to move each of scissor arms 1a and 1b in directions away from one another and out of the common plane of bone clamp 10, thereby disengaging ratchet cog 5 from teeth 4a. Although ratchet arm 4 is shown extending from scissor arm 1b in the preferred embodiment, it could instead be made integral with scissor arm 1a, and ratchet cog 5 be relocated on scissor arm 1b. In addition, scissor arm 1b is shown crossing over scissor arm 1a, but this may be reversed, for example in the case where the instrument is to be operated by a left-handed person, facilitating release of the ratchet mechanism.

A pin shaped clamp member 6 is connected at a terminal end of scissor arm 1a through a pin mounting pivot 7 extending crosswise therethrough. Pin shaped clamp member 6 is an elongated cylinder, with a sharp point 8 at its free end. A pin receiving clamp member 9 includes a tube portion 11, and a hooked portion 12 integral with or fixedly attached to tube portion 11 extending from a free end thereof. Tube portion 11 is an elongated cylindrical tube, open at both ends, and having an internal dimension for receiving pin shaped clamp member 6 therethrough. Because tube portion 11 serves as a guide track for slidable motion of pin shaped clamp member 6, there should not be excessive play between the outer diameter of pin shaped clamp member 6 and the inner diameter of tube portion 11, nor should the fit be too snug that smooth sliding motion is impeded. Pin receiving clamp member 9 is pivotally connected to scissor arm 3b through mounting pivot 13. Mounting pivot 13 does not however extend across tube portion 11 which would prevent the sliding motion of pin shaped clamp member 6 within tube shaped member 11. Instead, mounting pivot 13 is either fully external to tube portion 11 as is shown in FIG. 1, or oriented eccentric to the longitudinal clamp axis B of tube portion 11.

Hooked portion 12 extends from tube portion 11 and terminates in a sharp point 14. Sharp point 14 opposes sharp point 8 of pin shaped clamp member 6, and lies on a common longitudinal clamp axis B with sharp point 8 to provide stability when bone clamp 10 is closed. The sharp points 8 and 14 grip opposing surfaces of a fractured bone placed therebetween. Although, for purposes of disclosure, sharp points have been chosen as the means for gripping the surface of the bone to be reduced, it will be understood that any type of suitable surface configuration for biting bone may be used. For example, teeth may be used in place of single points. In addition, the teeth may have a wide base to fit a hole in a plate to be fastened to the bone, further enhancing performance of bone clamp 10, when such a plate is used to retain the correct alignment of the reduced fracture. It is also noted, with respect to the sliding mechanism of bone clamp 10, which in the case of the preferred embodiment comprises pin shaped clamp member 6 which is received within tube portion 11, that any suitable means of slidable mounting between each elongated clamp member pivotally mounted to, and extending from, the terminal ends of scissor arms 1a and 1b may be employed instead. Furthermore, where a pin received within a tube is used, the elongated components need not be cylindrical, as is disclosed with respect to the preferred case. For example, so long as the configurations of each are slidably engageable over the travel length thereof, the elements may be rectangular, or other suitable shape, in cross-section.

Bone clamp 10 is operated by inserting a thumb and an opposing finger of the same hand through finger loops 3a and 3b and closing scissor arms 1a and 1b by moving the fingers of the hand together. In response to the applied pressure, pin shaped clamp member 6 slides within tube portion 11 of pin receiving clamp member 9, closing the distance between sharp point 8 of pin shaped clamp member 6 and sharp point 14 of hooked portion 12 of pin receiving clamp member 9. Pin mounting pivot 7 and mounting pivot 13 allow the arcuate motion of scissor arms 1a and 1b to be transferred into linear sliding motion between pin shaped clamp member 6 and tube portion 11 of pin receiving clamp member 9. Ratchet cog 5 and ratchet arm 4 allows only stepwise movement in a closing direction, facilitating reduction by not allowing the fracture to widen once a particular degree of compression has been applied thereto, by stepwise advancement. In the preferred case, ratchet arm 4 is of sufficient length to still allow ratchet cog 5 to engage teeth 4a when pin shaped clamp member 6 is fully withdrawn into tube portion 11, bone clamp 10 being in a fully open position. The distance between scissor pivot 2 and the terminal ends of each of scissor arms 1a and 1b are preferably substantially the same length such that the longitudinal clamp axis B is approximately perpendicular to longitudinal scissor axis A. Furthermore, by making the distance between scissor pivot 2 and the terminal ends of scissor arms 1a and 1b shorter that the distance from scissor pivot 2 and finger loops 3a and 3b, an increase in mechanical advantage is obtained, facilitating application of increased pressure on the bone fracture.

Figure 7:
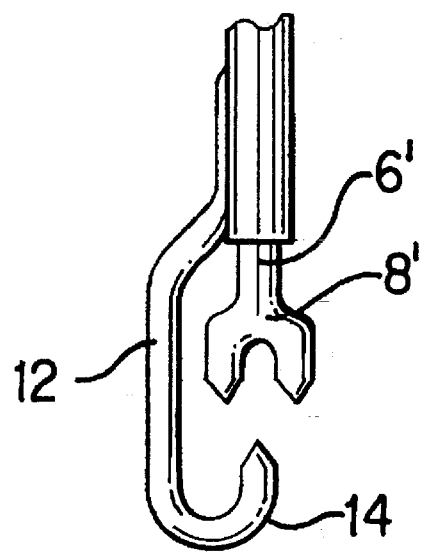
FIG. 7 is a detail of an embodiment of the bone clamp for three point fixation of a bone fracture.
Figure 8:
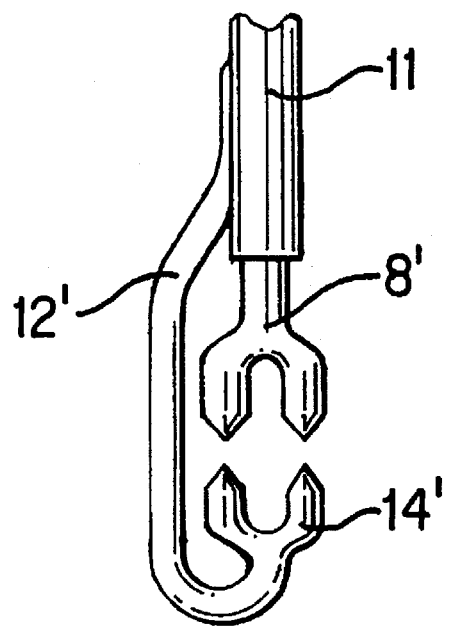
FIG. 8 is a detail of an embodiment of the bone clamp for four point fixation of a bone fracture.

Bone clamp 10, as described with reference to FIG. 1, utilizes two point fixation of the bone, i.e. two opposed and aligned points on either side of the bone. Alternatively, however, three, four or more point fixation may be desirable for certain applications. FIGS. 7 and 8 illustrate two possible configurations, illustrating 3 and four point fixation, respectively. In the embodiment of FIG. 7, pin shaped clamp member 6 is modified to include a pair of points 8' at a terminal end thereof (designated 6'), to provide two point contact on one side of the bone, and with single point 14 providing one point contact on the other side of the bone. In the embodiment of FIG. 8, a modified hooked portion 12' additionally includes two sharp points 14', which in combination with modified pin shaped clamp member 6', provide two point contact on both sides of the bone. Many additional configurations may be adopted to suit particular applications.

The bone clamp according to the present invention has been described with respect to the repair of small bone fractures, such as those occurring in the hand, because of its particular advantages in such application. However, it will be understood that the present invention may also be used with equal utility for the reduction of larger bones, such as the radius, ulna, humerus, fibula, tibia, femur, etc. while keeping the size of the required incision to a minimum. In such cases the dimensions of the bone clamp would be increased or changed appropriately.

Figure 2:
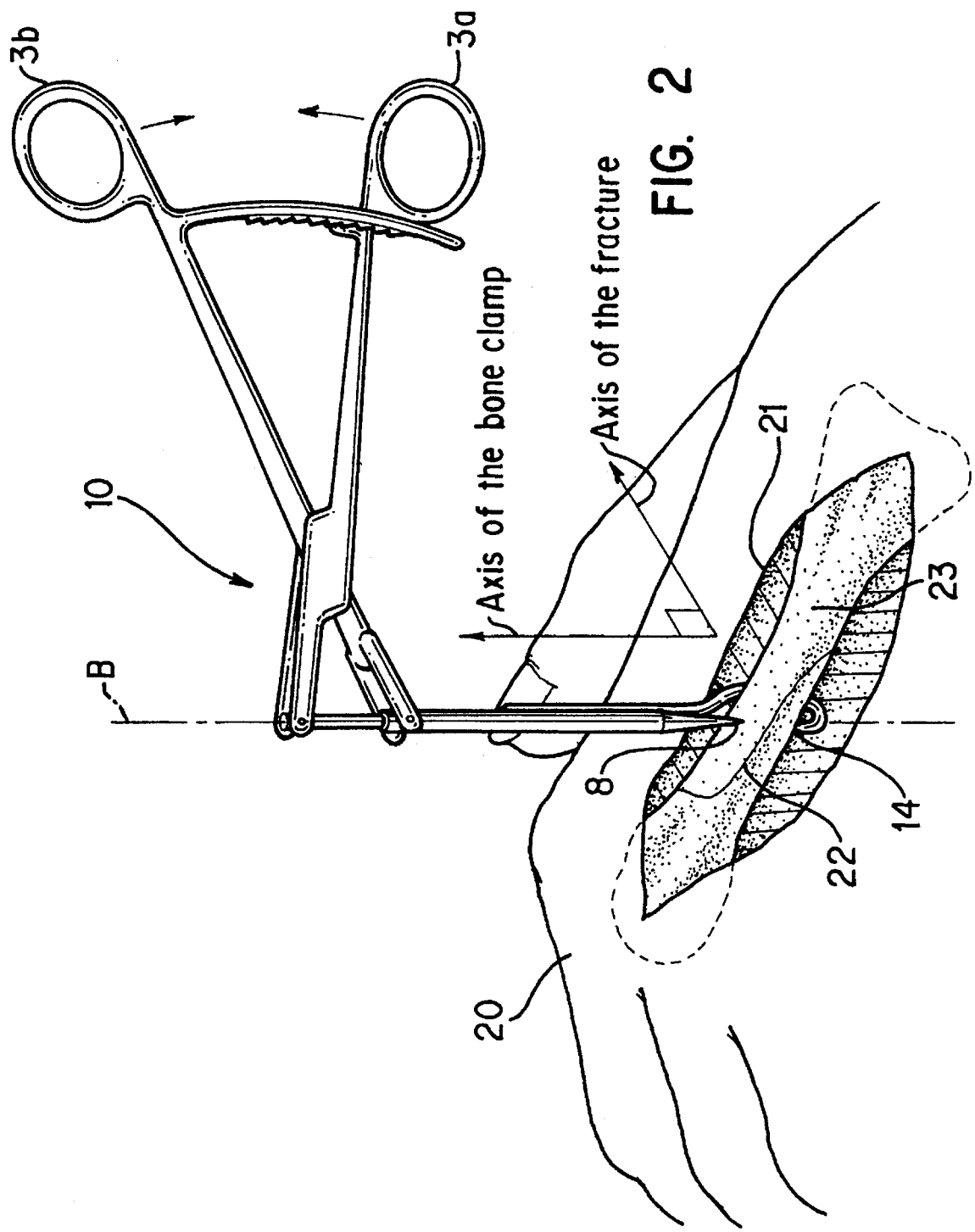
FIG. 2 is a perspective view of the bone clamp of FIG. 1 shown in use in repairing a metacarpal fracture of the hand.

Referring now to FIG. 2, bone clamp 10 according to the present invention is shown in use. Bone clamp 10 is inserted into an incision 21 in a hand 20 and oriented in position about a fracture 22 of a metacarpal 22. Longitudinal clamp axis is generally perpendicular to fracture 22, and sharp point 8 compresses from above and sharp point 12 from below, to reduce fracture 22 by application of hand pressure to urge finger loops 3a and 3b together, as shown by the arrows. Although not shown, a plate may be interposed between one of sharp points 8 and 12 and metacarpal 23 for affixing thereto to maintain proper alignment following removal of bone clamp 10.

Figure 3:
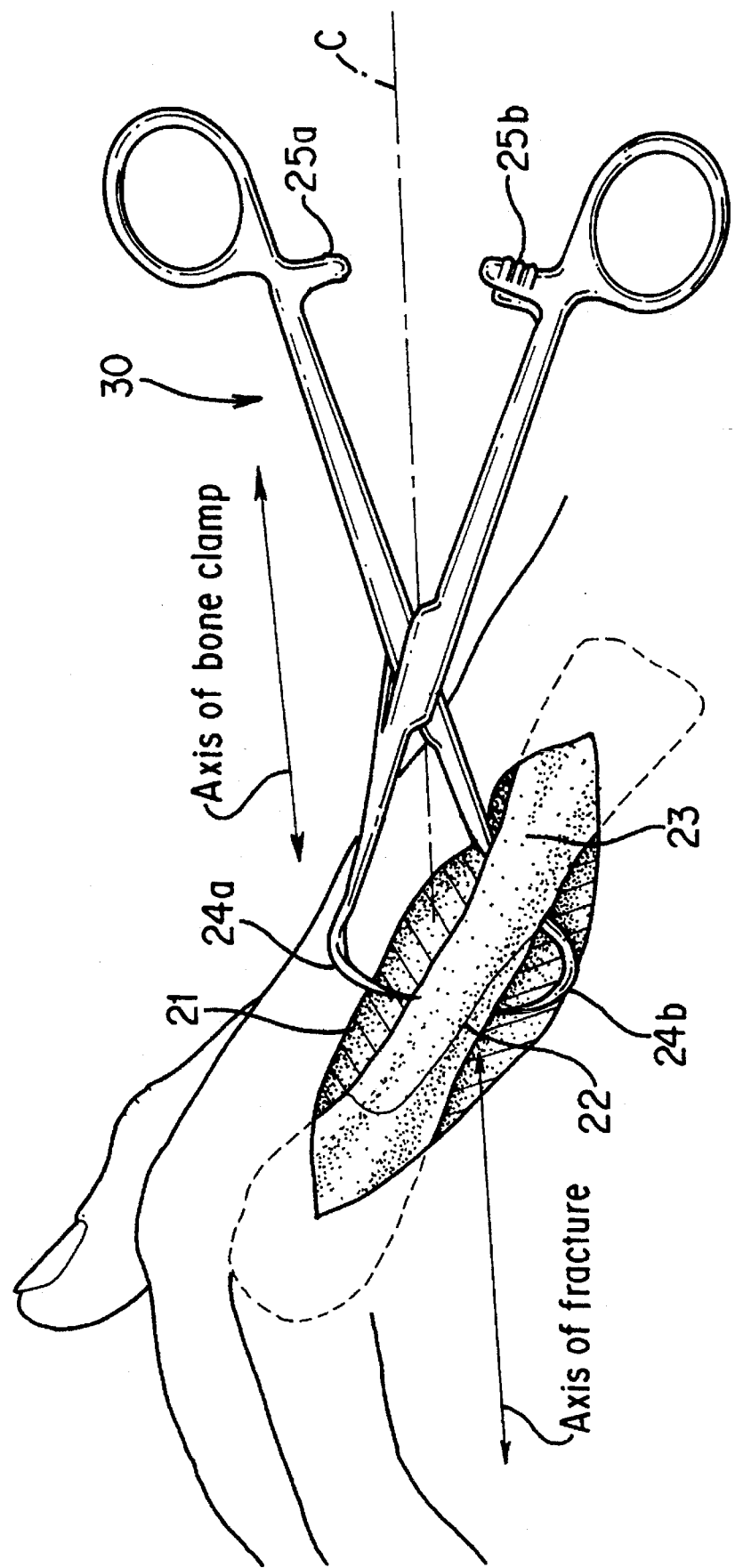
FIG. 3 is a perspective view of a prior art towel clip shown in use in repairing a metacarpal fracture of the hand.

FIG. 3 illustrates use of a prior art bone clamp, in particular a towel clip, generally designated 30, for purposes of contrast with the present invention. Longitudinal axis C of towel clip 30 is inserted into incision 21 and oriented parallel with fracture 22 in metacarpal 23. Curved tong portions 24a and 24b terminate in sharpened points which grip the metacarpal 23 therebetween to apply pressure to portions of the metacarpal 23 on opposite sides of the fracture. Because towel clip 30 must be inserted into incision 21 parallel to fracture 22, it requires more room than bone clamp 10, which is inserted perpendicularly, as shown in FIG. 2. Furthermore, as illustrated in FIG. 3, many towel clips have cooperating ratchet means 25a and 25b that are of insufficient arc as to permit their engagement when towel clip 30 is in an open position, since their intended purpose was for clamping towels in a sterile field, rather than bone.

Figure 5:
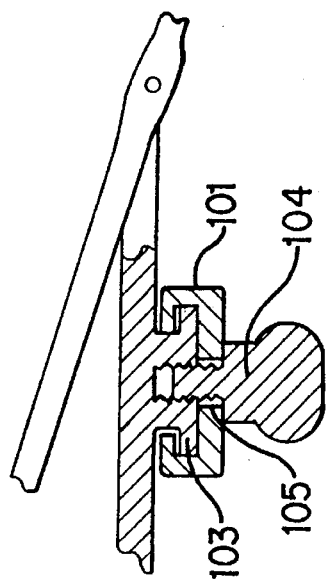
FIG. 5 is a partial cross sectional view taken on line V—V of FIG. 4.
Figure 6:
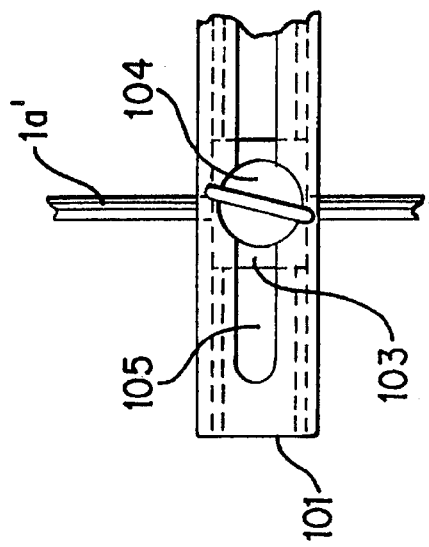
FIG. 6 is a bottom detail view of the bone approximator of FIG. 4, showing securement of a bone clamp to the slide bar.
Figure 4:
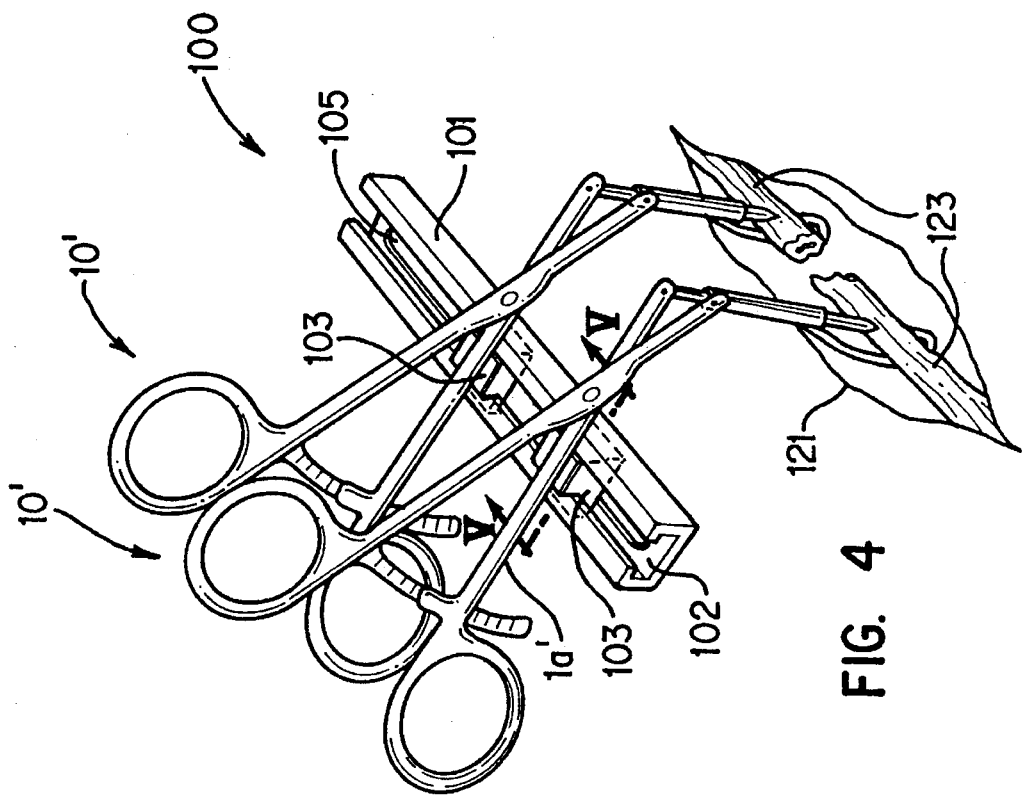
FIG. 4 is a perspective view of a bone approximator, utilizing a pair of bone clamps, in accordance with the present invention.

In addition to providing benefits relating to the repair of fractures requiring reduction, the bone damp as disclosed herein can further provide similar benefits in repairing fractures running crosswise the bone axis, requiring approximation. Referring now to FIGS. 4–6, a bone approximator is shown, generally designated 100. Bone approximator 100 includes a pair of bone clamps 10', at least one and preferably both of which are slidably mounted on a slide bar 101, with a plane of each substantially parallel with one another in the preferred case. Structure of bone clamps 10' is the same as bone clamp 10, described with reference to FIG. 1, with the addition of a mounting shoe 103 carried on a lower portion of a scissor arm 1a' (corresponding to scissor arm 1a of FIG. 1). It is noted that, although in the embodiment disclosed herein mounting shoe 103 is integral with scissor arm 1a', a suitably designed shoe may be removably attached to a bone clamp 10 of FIG. 1, to achieve a comparable structure and effect. Furthermore, although in the embodiment provides mounting means comprising mounting shoe 103 positioned on scissor arm 1a', bone clamps 10' may be mounted to slide bar 101 by a number of other means, which may be disposed at various other locations on bone clamp 10'.

A guideway 102 runs the length of slide bar 101, for slidably receiving mounting shoe 103 therein. Means are provided, preferably in the form of thumb screws 104 (one of which is shown in FIGS. 5 and 6), to secure bone clamps 10' at any desired position along slide bar 101. Mounting shoe 103 is threaded from below for receiving a threaded portion of thumb screw 104, which extends through a slot 105 which runs substantially the length of slide bar 101. Bone clamps 10' are secured at a desired location by tightening thumb screws 104 against the bottom of slide bar 101.

The procedure in which bone approximator 100 is used is as follows, described with reference to FIG. 4. The clamping ends of bone clamps 10' are inserted into a surgical incision 121, each aligned to clamp respective severed portions of a bone 123. Hand pressure is then applied to securely clamp bone segments 123. Bone clamps 10' are then moved along the slide bar as required to place the fractured ends in an anatomically correct alignment. When the desired positioning is achieved, bone clamps 10' are secured in place by tightening thumb screws 104 against slide bar 101. A plate (not shown) may then be affixed to the bones for bridging thereof, or other suitable procedure performed to maintain a union between bone segments 123. Upon completion of the mending procedure, gripping pressure of bone clamps 10' is released, and bone approximator 100 is removed from incision 121.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A bone clamp, comprising:

first and second scissor arms, each having a first and a second end, pivotally connected to one another at a scissor pivot point between said first and second ends thereof;

finger receiving means for communicating manual force, exerted on said first and second scissor arms by fingers in communication therewith, carried on said first end of each of said first and second scissor arms;

first and second clamp members;

said first clamp member being pivotally connected at a first end thereof to said second end of said first scissor arm and having a first gripping surface at a second end thereof aligned with a longitudinal axis of said first clamp member;

means for slidably mounting said second clamp member to said first clamp member permitting relative sliding movement of said first and second clamp members along said longitudinal axis, said second clamp member being pivotally connected at a first end thereof to said second end of said second scissor arm;

said second clamp member having a hooked portion at a second end thereof, said hooked portion including a second gripping surface on a terminal end thereof, in alignment with, and opposing said first gripping surface; and ratchet means for providing stepwise engagement of said first and second scissor arms from a position in which said finger receiving means are spaced apart to one in which said finger receiving means are brought closer together, while preventing movement in an opposite direction.

2. The bone clamp according to claim 1, wherein said first clamp member includes an elongated pin shaped member, and said second clamp member includes an elongated tube portion including means for receiving said pin shaped member therein.

3. The bone clamp according to claim 1, wherein a distance from said pivot point to each of said second ends of said first scissor arm and said second scissor arm are substantially the same.

4. The bone clamp according to claim 1, wherein said finger receiving means includes a pair of finger loops.

5. The bone clamp according to claim 1, wherein said first and second gripping surfaces are each a single sharp point.

6. The bone clamp according to claim 1, wherein one of said first and second gripping surfaces is a single sharp point, and a remaining one is at least two sharp points.

7. The bone clamp according to claim 1, wherein said first and second gripping surfaces are each at least two sharp points.

8. A bone clamp comprising:

first and second bone gripping members each having a bone engagement portion at first ends thereof;

means for slidably coupling said first and second bone gripping members to allow axial alignment of said bone engagement portions along a longitudinal axis of said first and second bone gripping members in an opposing relationship to clamp bone between said bone engagement portions;

first and second lever members, pivotally coupled together between first and second ends thereof;

means for coupling first ends of said first and second lever members with second ends of said first and second bone gripping members permitting relative longitudinal movement of said bone gripping members to be effected by a scissor action of said first and second lever members;

second ends of said first and second lever members having means for accepting fingers; and means for ratchetably coupling said first and second lever members.

9. The bone clamp according to claim 8, wherein said first bone gripping member includes an elongated pin shaped member, and said second bone gripping member includes an elongated tube portion including means for receiving said pin shaped member therein.

10. A bone approximator, comprising:

a slide bar;

a pair of bone clamps mounted on said slide bar, at least one of which is slidably mounted for movement over a range of positions on said slide bar;

means for securing each of said at least one bone clamp at any desired position in said range;

each of said pair of bone clamps including first and second scissor arms, each having a first and a second end, pivotally connected to one another at a scissor pivot point between said first and second ends thereof;

each of said pair of bone clamps further including finger receiving means for communicating manual force, exerted on said bone clamp by fingers in communication therewith, carried on said first end of each of said first and second scissor arms;

each of said pair of bone clamps further including first and second clamp members;

each of said pair of bone clamps further including said first clamp member being pivotally connected at a first end thereof to said second end of said first scissor arm and having a first gripping surface at a second end thereof aligned with a longitudinal axis of said first clamp member;

each of said pair of bone clamps further including means for slidably mounting said second clamp member to said first clamp member to permit relative sliding movement along said longitudinal axis, said second clamp member being pivotally connected at a first end thereof to said second end of said second scissor arm, said second clamp member having a hooked portion at a second end thereof, said hooked portion including a second gripping surface on a terminal end thereof, in alignment with, and opposing said first gripping surface; and each of said pair of bone clamps further including ratchet means for providing stepwise engagement of said first and second scissor arms from a position in which said finger receiving means are brought closer together, while preventing movement in an opposite direction.

11. The bone approximator according to claim 10, in which planes of said pair of bone clamps defined by intersection of said first and second scissor arms of each bone clamp are each substantially parallel with one another.

12. The bone approximator according to claim 10, in which both of said pair of bone clamps are slidably mounted on said slide bar.

13. The bone approximator according to claim 10, in which said at least one slidably mounted bone clamp further includes a mounting shoe integral therewith.

14. The bone approximator of claim 10 wherein one of said first and second scissors arms of said at least one slidably mounted bone clamp is slidably coupled to said slide bar.

\* \* \* \* \*